United States Patent
Namil et al.

(10) Patent No.: US 6,200,990 B1
(45) Date of Patent: Mar. 13, 2001

(54) NEUROPROTECTIVE AGENTS HAVING ANTIOXIDANT AND NMDA ANTAGONIST ACTIVITY

(75) Inventors: Abdelmoula Namil; Mark R. Hellberg, both of Arlington, TX (US)

(73) Assignee: Alcon Laboratories, Inc., Fort Worth, TX (US)

(*) Notice: Subject to any disclaimer, the term of this patent is extended or adjusted under 35 U.S.C. 154(b) by 0 days.

(21) Appl. No.: 09/460,869

(22) Filed: Dec. 14, 1999

Related U.S. Application Data

(60) Provisional application No. 60/113,258, filed on Dec. 21, 1998.

(51) Int. Cl.$^7$ ................. A61K 31/445; C07D 401/06; C07D 405/06

(52) U.S. Cl. .............. 514/320; 514/323; 546/196; 546/198

(58) Field of Search .................. 514/320, 323; 546/196, 198

(56) References Cited

U.S. PATENT DOCUMENTS

| | | |
|---|---|---|
| 4,550,022 | 10/1985 | Garabedian et al. ............. 424/127 |
| 4,638,070 | 1/1987 | Lembelin et al. ............... 549/23 |
| 4,690,931 | 9/1987 | Wick et al. .................. 514/317 |
| 5,597,809 | 1/1997 | Dreyer ...................... 514/37 |
| 5,604,244 | 2/1997 | DeSantis, Jr. et al. ........... 514/317 |

FOREIGN PATENT DOCUMENTS

| | | |
|---|---|---|
| 0 666 854 B1 | 3/1997 | (EP) . |
| 97/09308 * | 3/1997 | (WO) . |

OTHER PUBLICATIONS

Ambati, et al., Elevated GABA, Glutamate, and VEGF in the Vitreous of Humans With Proliferative Diabetic Retinopathy, *Invest. Ophthalmol. Vis. Sci.*, vol. 38, p. S771, #3234 (1997).
Benveniste et al, Elevation of the Extracellular Concentrations of Glutamate and Aspartate in Rat Hippocampus During transient Cerebral Ischemia Monitored by Intracerebral Microdialysis, *Journal of Neurochemistry*, vol. 43, No. 5, pp. 1369–1374 (1984).
Choi, Excitatory Cell Death, *Journal of Neurobiology*, vol. 23, No. 9, pp. 1261–1276 (1992).
Choi, Glutamate Neurotoxicity and Diseases of the Nervous System, *Neuron*, vol. 1, pp. 623–634 (1988).
David et al., Involvement of Excitory Neurotransmitters in the Damage Produced in Chick Embryo Retinas by Anoxia and Extracellular High Potassium, *Experimental Eye Research*, vol. 46, pp. 657–662 (1988).
Herndon et al., Ketanserin Aalogues: Structure–Affinity Relationship for 5–HT$_2$ and 5–HT$_{1C}$Serotonin Receptor Binding, *J. Med. Chem.* vol. 35, p. 4983 (1992).
Hudson, et al., Short–Wavelength and White–on–White Automated Static Perimetry in Patients With Clinically Significant Diabetic Macular Oedema (DMO), *Invest. Ophthalmol. Vis. Sci.*, vol. 38, p. S768, #3552 (1997).
Knöpfel et al., Metabotropic Glutamate Receptors: Novel Targets for Drug Development, *J. Med. Chem.*, vol. 38, No. 9, pp. 1417–1426 (1995).
Lieth, et al., Glial Glutamate to Glutamine Conversion is Impaired in Retinas of Diabetic Rats, *Invest. Ophthalmol. Vis. Sci.*, vol. 38, p. S695, #3571 (1997).
Massey, S., Cell types using glutamate as a neurotransmitter in the vertebrate retina, N.N. Osborne and G.J. Chader (Eds.) *Progress in Retinal Research*, Ch. 9, Pergammon Press: Oxford, 399–425 (1990).
Meldum, Possible therapeutic applications of antagonists of excitatory amino acid neurotransmitters, *Clinical Sci.*, vol. 68, pp. 113 (1985).
Miller et al., Excitatory amino acid receptors in the vertebrate retina, in *Retinal Transmitters and Modulators: Models for the Brain*, (W.W. Morgan, Ed.) CRC Press, Inc., Boca Raton, II:123–160 (1985).
Olney, John W., Excitotoxicity and N–Methyl–D–Asparate Receptors, *Drug Development Research*, vol. 17, pp. 299–319 (1989).
Olney et al., The Role of Specific Ions in Glutamate Neurotoxicity, *Neuroscience Letters*, vol. 65, pp. 65–71 (1986).
*Ophthalmic Surgery: Principles of Practice*, Ed., G.L. Spaeth, W.B. Sanders Co., Philadelphia, PA, U.S.A., pp. 85–87 (1990).
Scatton et al., Eliprodil Hydrochloride, *Drugs of the Future*, vol. 19, pp. 905–909 (1994).
Sheardown et al., 2,3–Dihydorxy–6–nitro–7–sulfamoyl–benzo(F) quinoxaline: A Neuroprotectant forCcerebral Ischemia, *Science*, vol. 247, pp. 571–574 (1990).
Siesjö, Calcium, Excitotoxins, and Brain Damage, *NIPS*, vol. 5, pp. 120–125 (1990).
Siliprandi et al., N–methyl–D–asparate–induced neurotoxicity in the adult rat retina, *Visual Neuroscience*, vol. 8, pp. 567–573 (1992).
Sisk et al., Histologic changes in the inner retina of albino rats following intravitreal injection of monosodium L–glutamate, *Graefe's Archive for Clinical and Experimental Ophthalmology*, vol. 223, pp. 250–258 (1985).
Sucher et al., N–methyl–D–aspartate Antagonists Prevent Kainate Neurotoxicity in Rat Retinal Ganglion Cells in vitro, *J. Neurosci.*, vol. 11, issue 4, pp. 966–971 (1991).
Tung et al., A quantitative analysis of the effects of excitatory neurotoxins on retinal ganglion cells in the chick, *Visual Neuroscience*, vol. 4, pp. 217–223 (1990).
Weiner, A.L., Polymeric Drug Delivery Systems For the Eye, in *Polymeric Site–specific Pharmacotherapy*, Ed., A.J. Domb, John Wiley & Sons, pp. 316–327 (1994).

* cited by examiner

*Primary Examiner*—Ceila Chang
(74) *Attorney, Agent, or Firm*—Sally S. Yeager

(57) ABSTRACT

The invention is directed to the use of novel compounds, compositions and methods for the prevention and treatment of neuronal tissue damage in mammals. The novel compounds comprise an antioxidant and a NMDA antagonist activity.

18 Claims, No Drawings

NEUROPROTECTIVE AGENTS HAVING ANTIOXIDANT AND NMDA ANTAGONIST ACTIVITY

This application claims priority to provisional application Ser. No. 60/113,258 filed Dec. 21, 1998.

The present invention relates to compounds, compositions and methods of use for the treatment of neural tissue diseases, disorders and injuries. The novel compounds have antioxidant and NMDA receptor antagonist activity. In particular, the methods of the present invention are useful in treating glaucoma, macular degeneration and other degenerative diseases of the eye, brain and spinal cord.

BACKGROUND OF THE INVENTION

Retinal or optic nerve head damage, which can result in the loss of vision, is caused by trauma and various pathological events including ischemia, hypoxia, or edema.

Retinal or optic nerve head ischemia or hypoxia results when blood supply is significantly reduced to these tissues. Ischemia is a complex pathological episode involving numerous biochemical events. In recent years, the involvement of excitatory amino acids in ischemia-related neuronal and retinal damage has been implicated. (See, e.g., Choi, Excitatory cell death, *Journal of Neurobiology*, volume 23, pages 1261–1276 (1992); Tung et al., A quantitative analysis of the effects of excitatory neurotoxins on retinal ganglion cells in the chick, *Visual Neuroscience*, volume 4, pages 217–223 (1990); Sisk et al., Histologic changes in the inner retina of albino rats following intravitreal injection of monosodium L-glutamate, *Graefe's Archive for Clinical and Experimental Ophthalmology*, volume 223, pages 250–258 (1985); Siliprandi et al., N-methyl-D-aspartate-induced neurotoxicity in the adult rat retina, *Visual Neuroscience*, volume 8, pages 567–573 (1992); and David et al., Involvement of excitatory neurotransmitters in the damage produced in chick embryo retinas by anoxia and extracellular high potassium, *Experimental Eye Research*, volume 46, pages 657–662 (1988).)

During ischemia or hypoxia, excitatory amino acids are markedly elevated (Benveniste et al, Elevation of the extracellular concentrations of glutamate and aspartate in rat hippocampus during transient cerebral ischemia monitored by intracerebral microdialysis, *Journal of Neurochemistry*, volume 43, pages 1369–1374 (1984)), the consequences of which may lead to excessive stimulation of post-synaptic excitatory amino acid receptors, and potentially resulting in cell injury. Antagonists against excitatory amino acid receptors have been shown to reduce neuronal and retinal damage in ischemic conditions. (See, e.g., Sheardown et al., 2,3-Dihydorxy-6-nitro-7-sulfamoyl-benzo(F) quinoxaline: a neuroprotectant for cerebral ischemia, *Science*, volume 247, pages 571–574 (1990); Scatton et al., Eliprodil Hydrochloride, *Drugs of the Future*, volume 19, pages 905–909 (1994); and Sucher et al., N-methyl-D-aspartate antagonists prevent kainate neurotoxicity in rat retinal ganglion cells in vitro, *Journal of Neuroscience*, volume 11, pages 966–971 (1991).) Release of excitatory amino acids has been demonstrated to cause cytotoxicity due to increases in intracellular calcium levels, which in turn affects protein phosphorylation, proteolysis, lipolysis, and ultimately causing cell death. (See, e.g., Choi, Glutamate neurotoxicity and diseases of the nervous system, *Neuron*, volume 1, pages 623–634 (1988); Siesjo, Calcium, excitotoxins, and brain damage, *NIPS*, volume 5, pages 120–125 (1990) and Olney et al., The role of specific ions in glutamate neurotoxicity, *Neuroscience Letters*, volume 65, pages 65–71 (1986).)

Diabetic retinopathy is an ophthalmic disease leading to loss of vision and even blindness. It has been reported that glutamate excitotoxicity has played a role in such vision loss. (See, e.g., Ambati, et al., Elevated GABA, Glutamate, and VEGF in the Vitreous of Humans With Proliferative Diabetic Retinopathy, *Invest. Ophthalmol. Vis. Sci.*, volume 38, page S771 (1997), (reported elevated levels of glutamate in vitreous samples obtained from patients with proliferative diabetic retinopathy who underwent pars plana vitrectomy. They suggested that these levels of glutamate are potentially toxic to retinal ganglion cells.); Lieth, et al., Glial Glutamate to Glutamine Conversion is Impaired in Retinas of Diabetic Rats, *Invest. Ophthalmol. Vis. Sci.*, volume 38, page S695 (1997), (reported that glial glutamate to glutamine conversion is impaired in the retinas of diabetic rats.); and Hudson, et al., Short-Wavelength and White-on-White Automated Static Perimetry in Patients With Clinically Significant Diabetic Macular Oedema (DMO), *Invest. Ophthalmol. Vis. Sci.*, volume 38, page S768 (1997), (reported deficits in retinal function related to ganglion cell function in patients with diabetic macular edema.)

Glutamate has also been recognized as a major excitatory neurotransmitter in the human central nervous system. It also has been demonstrated that exposure of neuronal cells to excessive levels of glutamate is neurotoxic (Knopfel et al., *J. Med. Chem.*, volume 38, no. 9, pages 1417–1426 (1995)). Thus, conditions which can lead to excessive glutamate release (e.g., traumatic brain injury, epilepsy, Parkinson's disease, senile dementia of the Alzheimer's type, cerebral or spinal cord ischemia, etc.) can lead to neurodegeneration. Agents which block glutamate receptors during excitotoxic events may provide protection against these diseases and conditions. The excitotoxin mechanism and the potential utilities of excitatory amino acid receptor antagonists have been described in the literature (see, e.g., Olney, *Drug Dev. Res.*, volume 17, page 299 (1988); and Meldum, *Clinical Sci.*, volume 68, pages 113 (1985).

There are at least three ionotropic neuronal receptors that have been named for the agonist that preferentially stimulates the receptor. These receptors have been classified as: N-methyl-D-aspartate (NMDA); kainate; and AMPA (2-amino-3-(3-hydroxy-5-methylisoxazol-4-yl)propanoic acid). These neuronal receptors are differentially distributed to specific cells in the retina. (See, generally, Massey, S., Cell types using glutamate as a neurotransmitter in the vertebrate retina, N. N. Osborne and G. J. Chader (Eds.) *Progress in Retinal Research*, Ch. 9, Pergammon Press: Oxford, 399–425 (1990); and Miller et al., Excitatory amino acid receptors in the vertebrate retina, in *Retinal Transmitters and Modulators: Models for the Brain*, (W. W. Morgan, Ed.) CRC Press, Inc., Boca Raton, II:123–160 (1985).) The localization of such receptors would account for the pathologies associated with glaucoma or inner retinal ischemia. For example, death of the retinal ganglion cell has to a large part been attributed to the NMDA receptor. (See, for example, Sucher et al., N-methyl-D-aspartate antagonists prevent kainate neurotoxicity in retinal ganglion cells in vitro, *J. Neurosci.*, volume 11, issue 4, pages 966–971 (1991).)

NMDA receptor antagonists have been pursued in the art for neuroprotection. For example, U.S. Pat. No. 4,690,931 (Wick et al.), U.S. Pat. No. 4,638,070 (Lembelin et al.), U.S. Pat. No. 5,306,723 (Chenard), U.S. Pat. No. 5,597,813 (Dreyer) and European Patent No. 666854 B1 disclose NMDA antagonists and methods of use. U.S. Pat. No. 5,604,244 (DeSantis) discloses intraocular irrigating solutions containing a polyamine antagonists (NMDA antagonists) and methods of use in treating retinal degeneration. None of these publications, however, disclose the novel compounds, compositions and methods of the present invention.

Given the numerous insults on a cell during ischemia and other trauma, the use of NMDA receptor antagonists alone may not provide the cytoprotective efficacy necessary to avoid necrosis. Compounds with broader inhibitory roles, i.e., compounds with dual pharmacophore efficacy may provide the added cytoprotective efficacy needed to prevent, reduce or ameliorate neuronal degradation.

SUMMARY OF THE INVENTION

The present invention is directed to compounds, compositions and methods of use for the treatment of eye, brain and spinal cord diseases. The compounds of the present invention possess NMDA antagonist and antioxidant activity. The methods involve administering to a human patient a composition comprising an effective amount of one or more compounds of the present invention.

The methods are particularly suited for the treatment of glaucoma, macular degeneration and other retinal diseases, as well as brain and spinal cord diseases.

DETAILED DESCRIPTION OF THE INVENTION

Insult to neural tissue (e.g., ischemia) can lead to an over-stimulation of the NMDA receptor. The over-stimulation of NMDA receptors leads to excitotoxicity. Ischemia and resultant excitotoxity eventually lead to neuronal cell death. The compounds of the present invention provide a two-pronged approach to treating neuronal degredation resulting from ischemia and excitotoxicity. The compounds possess both NMDA receptor antagonist and antioxidant activity.

The compounds of the present invention are of the formula (I):

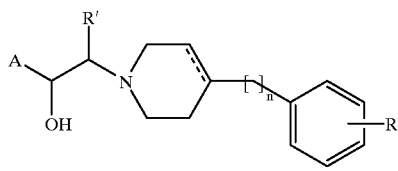

(I)

wherein:
A is

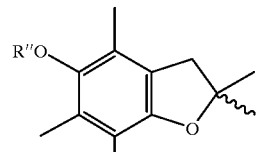

(a)

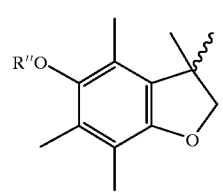

(b)

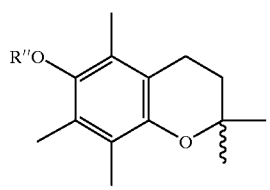

(c)

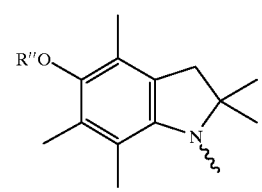

(d)

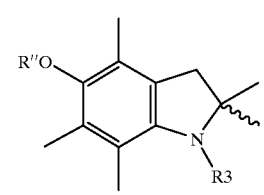

(e)

R is F, Cl, Br, OH, OR', $CF_3$ or R';
R' is H or $C_{1-6}$alkyl;
n is 0, 1 or 2;
R" is H, R'$CH_2$C(O)— or phosphate ester;
$R^3$ is R' or R'$CH_2$C(O)—; and
——————— is an optional bond.

The compounds of formula (I) also include various single stereoisomers or racemic mixtures of any of the compounds contemplated within formula (I), and pharmaceutically acceptable salts of the compounds of formula (I).

Preferred compounds of formula (I) are those compounds wherein:
A is (a), (b) or (c);
R' is H or $CH_3$;
R" is H or R'$CH_2$C(O)—; and
R is F, Cl or OH;

The most preferred compounds of formula (I) are the following compounds:
A is (a) or (c);
R' is H or $CH_3$;
R" is H or $CH_3$C(O)—;
R is F, Cl or OH;
n is 0 or 1; and
R is F or OH.

Preferred compounds of the present invention are:

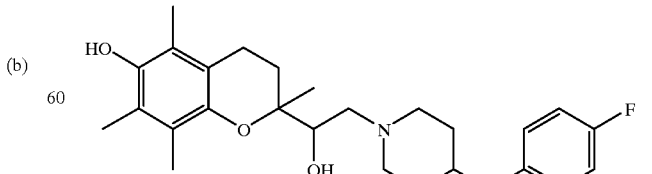

1-[(6-hydroxy-3,4 dihydro-2,5,7,8-tetramethyl-2H-1-benzopyran-2yl)]-2-[4-(4-fluorobenzyl)piperidin-1-yl]

ethanol hydrochloride ("Compound 1")

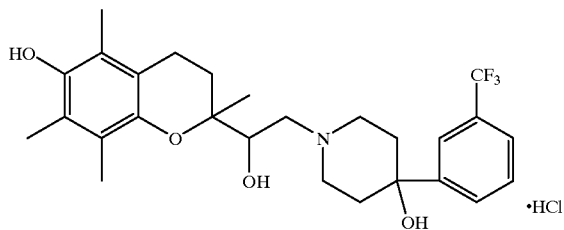

1-[(6-hydroxy-3,4 dihydro-2,5,7,8-tetramethyl-2H-1-benzopyran-2yl)]-2-[4-hydroxy-(4(3-trifluoromethylphyenyl)piperidin-1-yl]ethanol hydrochloride ("Compound 2")

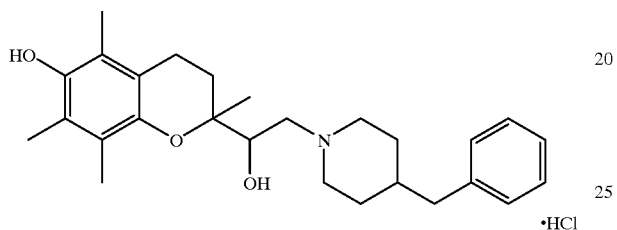

1-[(6-hydroxy-3,4 dihydro-2,5,7,8-tetramethyl-2H-1-benzopyran-2yl)]-2-[4-(benzylpiperidin-1-yl]ethanol hydrochloride ("Compound 3")

The following Examples 1–3 are synthesis examples of preferred compounds of the present invention:

EXAMPLE 1

1-[(6-Hydroxy-3,4 dihydro-2,5,7,8-tetramethyl-2H-1-benzopyran-2-yl)]-2-[4-(4-fluorobenzyl)piperidinyl]ethanol hydrochloride was made by a multiple step procedure from Trolox® (1-[benzopyran-(6-hydroxy-3,4-dihydro-2,5,7,8-tetramethyl-2H)-2-carboxylic acid).

Step 1

Preparation of Benzyl (6-benzyloxy-3,4-dihydro-2, 5,7,8-tetramethyl-2H-1-benzopyran-2-yl)carboxylate intermediate To a solution of Trolox® (10 g, 39.1 mmol) at) at 0° C. in DMF (50 mL), was added sodium hydride (60% dispersion in oil, 3.5 g, 87.9 mmol). The reaction mixture was stirred at 0° C. for 15 minutes and then benzyl bromide (17.1 g, 99.9 mmol) was added drop wise. The reaction mixture was allowed to warm to room temperature and stirred for overnight. DMF was evaporated under high vacuum and then the residue was dissolved in ethyl acetate (200 mL) and washed with 1 N aqueous HCl (100 mL) and brine (100 mL) to give 10.1 g (58.7%) of an oil of the intermediate, benzyl (6-benzyloxy-3,4-dihydro-2,5,7,8-tetramethyl-2H-1-benzopyran-2-yl)carboxylate. $^1$H NMR (CDCl$_3$) δ1.57 (s, 3H), 1.82 (m, 1H), 2.02 (s, 3H), 2.08 (s, 3H), 2.15 (s, 3H), 2.44 (m, 3H), 4.61 (s, 2H), 5.00 (q, 2H), 7.00–7.45 (m, 10H). MS(ES) m/z 431.

Step 2

Preparation of (6-Benzyloxy-3-4-dihydro-2,5,7,8-tetramethyl-2H-1-benzopyran-2-yl)methanol intermediate.

To a solution of benzyl (6-benzyloxy-3,4-dihydro-2,5,7, 8-tetramethyl-2H-1-benzopyran-2-yl)carboxylate (5 g, 11.62 mmol) in THF (100 mL) was added 23 mL of LAH (1.0 M solution in THF). The mixture was stirred at room temperature for 1 hour and then the excess of reagent was destroyed by adding 100 mL of ethyl acetate followed by 60 mL of 1.0 M solution of aqueous HCl. The organic layer was separated and evaporated to give 2.5 g (66 %) of the (6-Benzyloxy-3-4-dihydro-2,5,7,8-tetramethyl-2H-1-benzopyran-2-yl)methanol intermediate. $^1$H NMR (CDCl$_3$) δ1.24 (s, 3H), 1.70–198 (m, 2H), 2.11 (s, 3H), 2.18 (s, 3H), 2.23 (s, 3H), 2.66 (m, 2H), 3.63 (m, 2H), 4.70 (s, 2H), 7.29–7.53 (m, 5H). MS(ES) m/z 327.

Step 3

Preparation of (6-Benzyloxy-3,4-dihydro-2,5,7,8-tetramethyl-2H-1-benzopyran-2-yl)carboxaldehyde intermediate (6-Benzyloxy-3-4-dihydro-2,5,7,8-tetramethyl-2H-1-benzopyran-2-yl)methanol (4.26 g, 13.07 mmol) was dissolved in a mixture of dichloromethane-water (100 mL, (v/v)) at 0° C. To this solution was added Na$_2$CO$_3$ (0.89 g, 8.39 mmol), NaHCO$_3$ (6.88 g, 81.90 mmol), tetrabutyl ammonium chloride (0.82 g, 2.95 mmol), 2,2,6,6-tetramethyl-1-piperidinyloxy, free radical (0.47 g, 3.01 mmol), and N-chlorosuccinamide (2.72 g, 20.4 mmol). The reaction mixture was vigorously stirred for 30 minutes and then warmed to room temperature and stirred for an additional 2 hours. The reaction mixture was quenched by adding a mixture of water and dichloromethane (200 mL (v/v)). The organic layer was separated, dried (MgSO$_4$) and the solvent was evaporated to give an oil of (6-Benzyloxy-3,4-dihydro-2,5,7,8-tetramethyl-2H-1-benzopyran-2-yl)carboxaldehyde intermediate which was purified by flash chromatography using (ethyl acetate-hexane (9:1)) to give 2.6 g (61.5%). $^1$H NMR (CDCl$_3$) δ1.41 (s, 3H), 1.82 (m, 1H), 2.11 (s, 3H), 2.13 (s, 3H), 2.17 (s, 3H), 2.27 (m, 1H), 2.58 (m, 2H), 4.69 (s, 2H), 7.34–7.52 (m, 5H), 9.64 (s, 1H). MS(ES) m/z 325.

Step 4

(6-Benzyloxy-3,4-dihydro-2,5,7,8-tetramethyl-2H-1-benzopyran-2-yl)ethoxide intermediate In a round bottom flask was placed sodium hydride (60% oil dispersion, 0.41 g, 10.19 mmol) and trimethyl sulfoxonium iodide (2.45 g, 11.10 mmol). The reaction mixture was stirred at 0° C. for 15 min and then allowed to warm to room temperature and stirred for an additional 15 minutes. To this solution was added (6-Benzyloxy-3-4-dihydro-2,5,7,8-tetramethyl-2H-1-benzopyran-2-yl)carboxaldehyde (3 g, 9.3 mmol) and then the reaction mixture was stirred at room temperature for 30 minutes and warmed to 60° C. and stirred for an additional 30 minutes. The reaction mixture was then cooled down, diluted with 100 mL of water and extracted with ethyl acetate (2×100 mL). Ethyl acetate layer was dried (MgSO$_4$), concentrated under vacuum to give an oil of (6-Benzyloxy-3,4-dihydro-2,5,7,8-tetramethyl-2H-1-benzopyran-2-yl)ethoxide which was purified by flash chromatography using ethyl acetate-hexane (9:1) to afford 1.8 g (70.6%).

$^1$H NMR (CDCl$_3$) δ1.22 (m, 7H), 1.78–1.95 (m, 1H), 2.02 (s, 3H), 2.10 (s, 3H), 2.14 (s, 3H), 2.57–2.67 (m, 2H), 4.62 (s, 2H), 7.34–7.52 (m, 5H). MS(ES) m/z 339.

Step 5

Preparation of the title compound, 1-[(6-Hydroxy-3, 4 dihydro-2,5,7,8-tetramethyl-2H-1-benzopyran-2-yl)]-2-[4-(4-fluorobenzyl)piperidinyl]ethanol hydrochloride (Compound 1)

A solution of (6-Benzyloxy-2,5,7,8 tetramethyl-3,4-dihydro-2H-1-benzopyranyl)-2-ethoxide (0.58 g, 1.72 mmol) and 4-(4-fluorobenzyl)piperidine (1.16 g, 6 mmol), prepared as described by Herndon et al. *J. Med. Chem.* Volume 35, page 4983 (1992), in DMF (10 mL) was refluxed for 48 hours. DMF was evaporated under vacuum and then the residue was dissolved in methanol (40 mL). To this solution was added ammonium formate (0.43 g, 6.82 mmol) and 300 mg of Pd/C (10%). The reaction mixture was then refluxed for 12 hours, filtered over celite, and then the volatiles were evaporated. The oily residue was purified by flash chromatography using dichloromethane-methanol (9:1). The free base was obtained, 100 mg (13.3%), and then was dissolved in ether and transformed to its corresponding hydrochloride salt, 1-[(6-Hydroxy-3,4 dihydro-2,5,7,8-tetramethyl-2H-1-benzopyran-2-yl)]-2-[4-(4-fluorobenzyl)piperidinyl]ethanol hydrochloride, by adding 1.0 M solution of hydrogen chloride in diethyl ether. Mp: 105–1080° C. MS(ES) m/z 442. CHN for ($C_{27}H_{37}FNO_3Cl+1H_2O$). Calculated: C,65.37; H,7.92; N,2.82. Found: C,65.41; H,7.92; N,3.13.

EXAMPLE 2

Preparation of 1-[(6-Hydroxy-3,4-dihydro-2,5,7,8-tetramethyl-2H-1-benzopyran-2-yl)]-2-[4-hydroxy-(4-(3-trifluoromethylphenyl)piperidin-1-yl]ethanol hydrochloride (Compound 2)

This compound was prepared by methods analogous to the Example 1 methods, by substituting 4-hydroxy-(4-(3-trifluoromethylphenyl)piperidine for 4-(4-fluorobenzyl)piperidine in Step 5, to give an 18% yield.

$^1$H NMR (DMSO, $d_6$) δ1.15 (d, 3H), 1.78–1.95 (m, 4H), 2.02–2.13 (m, 8H), 2.50 (m, 6H), 3.33–3.52 (m, 6H), 4.04 (m, 1H), 5.78 (m, 2H), 7.65–7.82 (m, 4H), 9.91 (bs, 1H). m/z) 494.

CHN for ($C_{27}H_{35}F3NO_3Cl+0.5H_2O$). Calculated: C,60.16; H,6.73; N, 2.60. Found: 60.24; H,6.60; N,2.60.

EXAMPLE 3

Preparation of 1-[(6-hydroxy-2,5,7,8-tetramethyl-3,4-dihydro-2H-1-benzopyran-2-yl)]-2-[(4-benzylpiperidin-1-yl]ethanol hydrochloride (Compound 3)

This compound was prepared by methods analogous to the Example 1 methods, by substituting 4-benzylpiperidine for 4-(4-fluorobenzyl)piperidine in Step 5, to give a 24% yield.

Mp 188–190° C. $^1$H NMR (DMSO, $d_6$) δ1.15 (s, 3H), 1.51–1.72 (m, 6H), 2.02–2.13 (m, 8H), 2.50–255 (m, 5H), 2.67–3.15 (m, 6H), 3.53 (m, 2H), 3.95 (m, 1H), 5.75 (m, 1H), 7.17–7.44 (m, 5H), 9.49 (bs, 1H). MS(ES) m/z 424.

CHN for ($C_{27}H_{38}NO_3Cl+0.2H_2O$). Calculated: C,69.94; H,8.35; N,3.02. Found: C,69.94; H,8.33; N,2.87.

As stated above, the methods of the present invention are directed to the treatment of ophthalmic, spinal cord and brain diseases, disorders or injuries.

The methods of the present invention are particularly directed to the use of compounds of formula (I) for the treatment of diseases, disorders or injuries of the eye, including, but not limited to, age related macular degeneration, retinitis pigmentosa, retinal detachments, retinal ischemia, acute retinopathies associated with trauma, inflammatory mediated degenerations, post-surgical complications, the damage associated with laser therapy including photodynamic therapy (PDT), and surgical light induced iatrogenic retinopathy.

The methods of the present invention are also directed to the treatment of brain diseases, disorders or injuries, including, but not limited to, stroke, head trauma, epilepsy and other seizure disorders, Alzheimer's disease, Huntington's diseases and other diseases where excitotoxic events are known to participate. The methods of the present invention are also directed to the treatment of spinal cord diseases, disorders or injuries, including Lou Gehrig's disease (ALS) and other diseases where excitotoxic events are known to participate.

The compositions of the present invention will include one or more compounds of formula (I) and a pharmaceutically acceptable vehicle for the compound(s).

The compounds of formula (I) may be formulated for acute or chronic administration. In the case of acute administration, the compounds of formula (I) will be preferably administered intraocularly, intracerebrally or intraspinally following traumatic and/or other acute ischemic events involving the respective tissues or prior to or during surgery to prevent ischemic damage or injury.

With regard to ophthalmic applications, the compounds of formula (I) of the present invention may be contained in various types of pharmaceutical compositions, in accordance with formulation techniques known to those skilled in the art. In general, the compounds of formula (I) will be formulated in solutions for topical ophthalmic, intraocular or systemic administration. Solutions, suspensions and other dosage forms adapted for intraocular injection or perfusion, such as balanced salt solutions, are particularly preferred for the acute treatment of retinal and optic nerve head tissues.

Topical ophthalmic compositions will be employed when the compounds are to be dosed topically. The preparation of topical ophthalmic compositions is well known in the art. Generally, topical ophthalmic compositions useful in the present invention will be in the form of a solution, suspension, gel, or formulated as part of a device, such as a collagen shield or other bioerodible or non-bioerodible device. Various excipients may be contained in the topical ophthalmic solutions, suspensions or gels of the present invention. For example, buffers (e.g., borate, carbonate, phosphate), tonicity agents (e.g., sodium chloride, potassium chloride, polyols), preservatives (e.g., polyquaterniums, polybiguanides, BAC), chelating agents (e.g., EDTA), viscosity enhancing agents (e.g., polyethoxylated glycols) and solubilizing agents (e.g., polyethoxylated castor oils, including polyoxl-35 castor oil (Cremophor EL®, BASF Corp., Parsippany, N.J.); Polysorbate 20, 60 and 80; Pluronic® F-68, F-84 and P-103 (BASF Corp.); or cyclodextrin) may be included in the topical ophthalmic compositions. A variety of gels may be useful in topical ophthalmic gel compositions of the present invention, including, but not limited to, carbomers, polyvinyl alcohol-borates complexes, or xanthan, gellan, or guar gums. Topical ophthalmic bioerodible and non-bioerodible devices (e.g., conjunctival implant) are known in the art and may be useful in the topical administration of formula (I) compounds. See, for example, Weiner, A. L., Polymeric Drug Delivery Systems For the Eye, in *Polymeric Site-specific Pharmacotherapy*, Ed., A. J. Domb, John Wiley & Sons, pages 316–327 (1994). While the particular ingredients and amounts to be contained in topical ophthalmic compositions useful in the methods of the present invention will vary, particular topical ophthalmic compositions will be formulated to effect the administration of a compound of formula (I) topically to the eye.

When the compounds of formula (I) are administered during intraocular, intracerebral or intraspinal surgical procedures, such as through retrobulbar or periocular injection, intraocular perfusion or injection, or intraspinal or intracerebral injection or perfusion, the use of irrigating solutions as vehicles are most preferred. The most basic irrigating solutions generally comprise saline, or phosphate-buffered saline. More advanced irrigating solutions, however, are preferred. As used herein, the term "physiologically balanced irrigating solution" refers to a solution which is adapted to maintain the physical structure and function of tissues during invasive or noninvasive medical procedures. This type of solution will typically contain electrolytes, such as sodium, potassium, calcium, magnesium and/or chloride; an energy source, such as dextrose; and a bicarbonate-buffer to maintain the pH of the solution at or near physiological levels. Various solutions of this type are known (e.g., Lactated Ringers Solution). BSS® Sterile Irrigating Solution and BSS Plus® Sterile Intraocular Irrigating Solution (Alcon Laboratories, Inc., Fort Worth, Tex. USA) are examples of physiologically balanced intraocular irrigating solutions. The latter type of solution is described in U.S. Pat. No. 4,550,022 (Garabedian, et al.), the entire contents of which are incorporated herein by reference. Retrobulbar and periocular injections are known to those skilled in the art and are described in numerous publications including, for example, *Ophthalmic Surgery: Principles of Practice,* Ed., G. L. Spaeth, W. B. Sanders Co., Philadelphia, Pa., U.S.A., pages 85–87 (1990).

Systemic compositions of the present invention can be formulated by well known techniques in the art. Oral compositions will generally be in the form of tablets, hard or soft gelatin capsules, suspensions, granules, powders or other typical compositions and will contain excipients typically present in such compositions. Methods for the preparation of such oral vehicles are well known by those skilled in the art. Parenteral administration compositions will be generally be in the form of injectable solutions or suspensions. Methods for the preparation of such parenteral compositions are well known by those skilled in the art.

In general, the formula (I) concentrations of the compositions and the doses used for the above described purposes will vary, but will be in an effective amount to prevent, reduce or ameliorate neuronal tissue damage. As used herein, "therapeutically effective amount" refers to an amount of at least one compound of formula (I) which will prevent, reduce or ameliorate neuronal tissue damage in a mammal. In general, irrigation solutions will contain one or more of the compounds of formula (I) in a concentration of from about 0.01 $\mu$M to about 100 $\mu$M. The volume of irrigation solution administered will depend on the administrative procedure, e.g., intraocular irrigation, or intraocular or intracerebral injection, and the particular condition being treated. Topical ophthalmic compositions will generally have a formula (I) compound concentration of from about 0.01%–1.0% w/v. Patients receiving topical doses will be dosed with about 1–2 drops of a topical ophthalmic composition, about 1–4 times per day.

In the systemic treatment of conditions including, but not limited to, stroke, traumatic brain injury, neurodegenerative disorders, Parkinson's disease, Alzheimer's disease, Lou Gehrig's disease, glaucoma and retinopathies, the patient will generally be dosed with a compound of formula (1) in an amount of about 0.02 to 10 mg/kg/day in single or divided doses, regardless of the route of administration (i.e., oral, parenteral (s.c., i.m., i.v.)). Systemic treatments involving the oral route of administration are preferred.

Any of the above-described vehicles or other vehicles known in the art may be employed in the compositions of the present invention, provided such vehicles allow for the administration of a compound of formula (I) to the tissue to be treated and do not cause significant side effects to the patient. As used herein, such a vehicle is referred to as a "pharmaceutically acceptable vehicle."

The compositions of the present invention may contain additional pharmaceutically active agents or may be dosed concurrently with other pharmaceutical compositions. In particular, when treating a mammal for the prevention, treatment or amelioration of glaucomatous retinopathy, the compositions of the present invention may contain additional "anti-glaucoma" agents or may be dosed concurrently or sequentially with anti-glaucoma agent compositions. Examples of anti-glaucoma agents include: prostaglandins or prostanoids, carbonic anhydrase inhibitors, beta-adrenergic agonists and antagonists, alpha-adrenergic agonists or other anti-glaucoma agents known to those skilled in the art.

EXAMPLE 4

The following is an example of a oral tablet which may be prepared by conventional tableting techniques:

| Ingredient | Amount |
| --- | --- |
| Compound of formula (I) | 5.0 mg |
| Lactose | 67.8 mg |
| Avicel ® | 31.5 mg |
| Amberlite ® | 1.0 mg |
| Magnesium Stearate | 0.25 gm |

EXAMPLE 5

The following is an example of a topical ophthalmic formulation of the present invention:

| Ingredient | Amount (wt %) |
| --- | --- |
| Compound of formula (I) | 0.1 |
| Polyvinyl alcohol | 1.4 |
| Monobasic sodium phophate, Monohydrate | 0.05 |
| Dibasic Sodium Phophate, (Anhydrous) | 0.15 |
| Sodium Chloride | 0.5 |
| Disodium EDTA | 0.01 |
| Polysorbate 80 | 0.05 |
| Benzalkonium Chloride, Solution | 0.01 + 5% excess |
| Sodium Hydroxide, Hydrochloric Acid | q.s. |
| Water | q.s. |

The invention in its broader aspects is not limited to the specific details shown and described above. Departures may be made from such details within the scope of the accompanying claims without departing from the principles of the invention and without sacrificing its advantages.

What is claimed is:

1. A compound of formula (I):

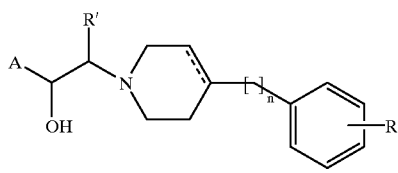

wherein:

A is (a) 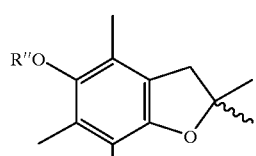

(b) 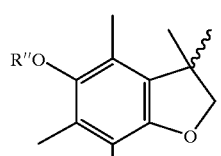

(c) 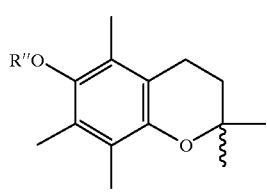

(d) 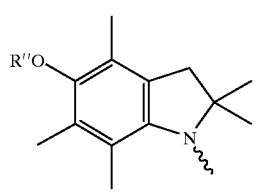

(e) 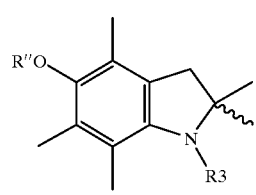

R is F, Cl, Br, OH, OR', CF₃ or R';
R' is H or C$_{1-6}$alkyl;
n is 0, 1 or 2;
R" is H, R'CH₂C(O)— or phosphate ester;
R3 is R' or R'CH₂C(O)— and
——— is an optional bond.

2. A compound according to claim 1, wherein:
A is (a), (b) or (c);
R' is H or CH₃;
R" is H or R'CH₂C(O)—; and
R is F, Cl or OH.

3. A compound according to claim 1, wherein:
A is (a) or (c);
R' is H or CH₃;
R" is H or CH₃C(O)—;
R is F, Cl or OH;
n is 0 or 1; and
R is F or OH.

4. A compound according to claim 1, wherein the compound is selected from the group consisting of:

(b) 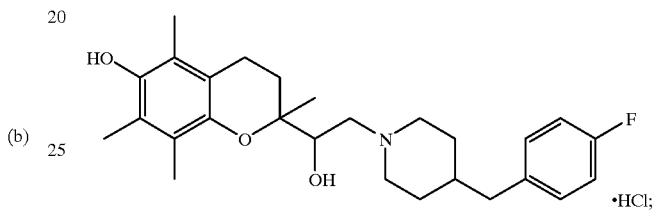
•HCl;

(c) 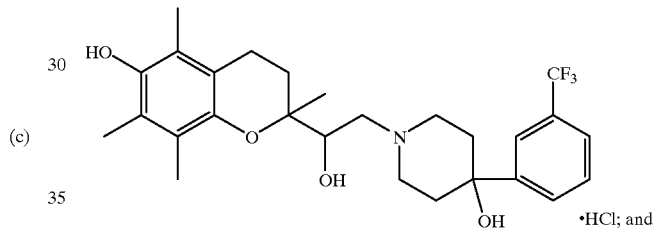
•HCl; and (d) 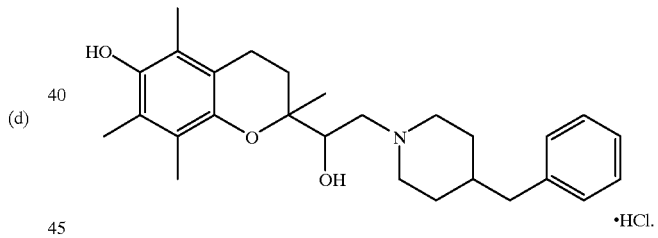
•HCl.

5. A composition for the treatment of an ophthalmic, brain or spinal cord disease, disorder or injury comprising a pharmaceutically acceptable vehicle and a NMDA receptor antagonistic effective amount of one or more compounds of formula (I):

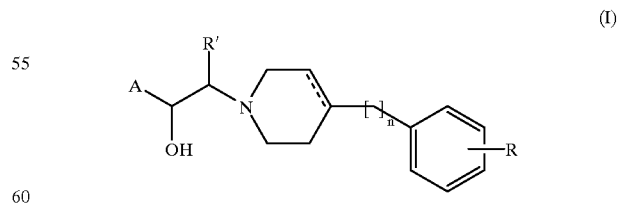

wherein:

A is

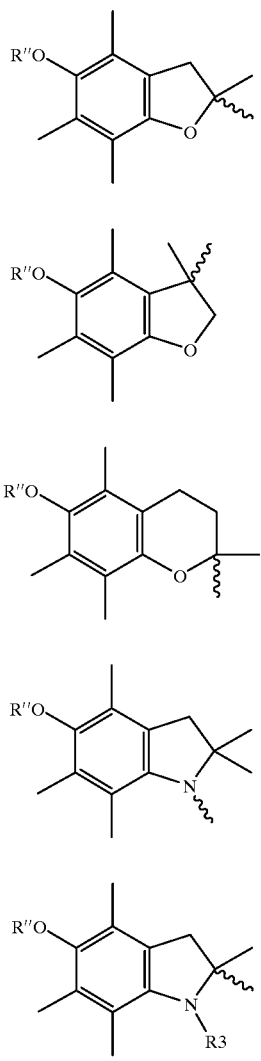

(a)

(b)

(c)

(d)

(e)

R is F, Cl, Br, OH, OR', CF₃ or R';
R' is H or $C_{1-6}$alkyl;
n is 0, 1 or 2;
R" is H, R'CH₂C(O)— or phosphate ester;
R3 is R' or R'CH₂C(O)— and
――― is an optional bond.

6. A composition according to claim 5, wherein:
A is (a), (b) or (c);
R' is H or CH₃;
R" is H or R'CH₂C(O)—; and
R is F, Cl or OH.

7. A composition according to claim 5, wherein:
A is (a) or (c);
R' is H or CH₃;
R" is H or CH₃C(O)—;
R is F, Cl or OH;
n is 0 or 1; and R is F or OH.

8. A compound according to claim 5, wherein the compound is selected from the group consisting of:

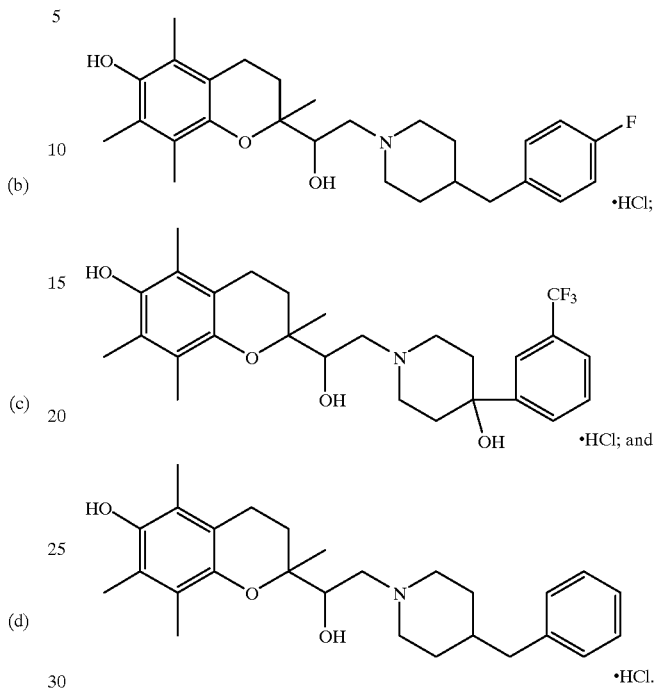

9. A composition according to claim 5, wherein the composition is a systemic, topical or intraocular or intracerebral composition.

10. A method of treating a pathological condition, in the brain, eye or spinal cord which was resulted from over stimulation of the NMDA receptor, of a mammal in need thereof, comprising administering to said mammal a NMDA receptor antagonistic effective amount of one or more compounds of formula (I):

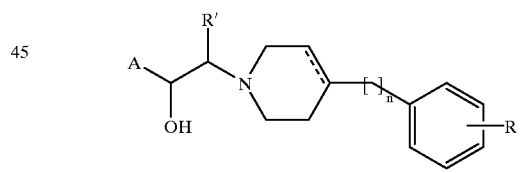

(I)

wherein:

A is (a)

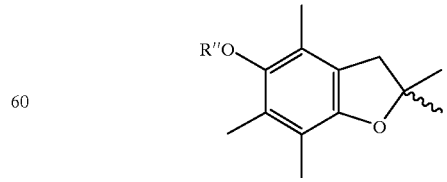

-continued

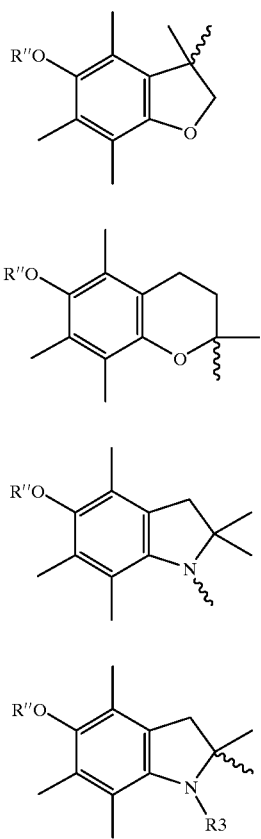

R is F, Cl, Br, OH, OR', CF₃ or R';
R' is H or C$_{1-6}$alkyl;
n is 0, 1 or 2;
R" is H, R'CH₂C(O)— or phosphate ester;
R3 is R' or R'CH₂C(O)— and
────── is an optional bond.

11. A method according to claim 10, wherein:
A is (a), (b) or (c);
R' is H or CH₃;
R" is H or R'CH₂C(O)—; and
R is F, Cl or OH.

12. A method according to claim 10, wherein:
A is (a) or (c);
R' is H or CH₃;
R" is H or CH₃C(O)—;
R is F, Cl or OH;
n is 0 or 1; and R is F or OH.

13. A method according to claim 10, wherein the compound is selected from the group consisting of:

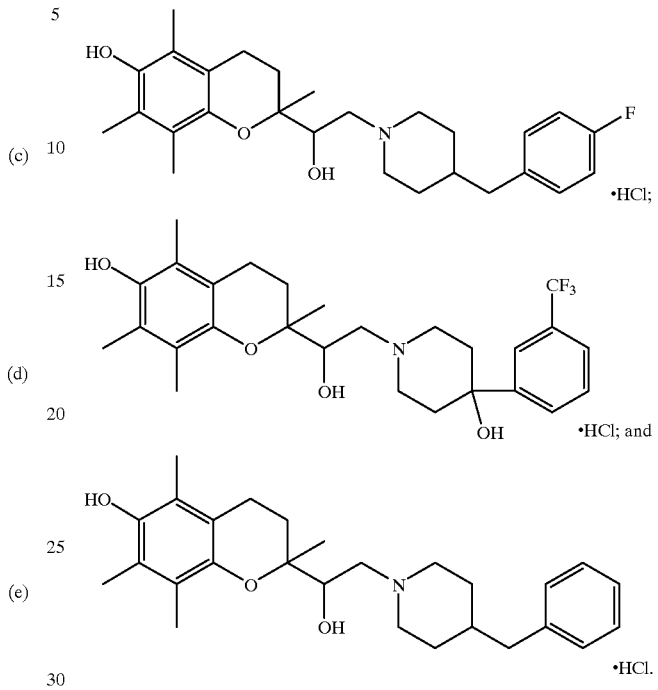

14. A method according to claim 10, wherein the composition is a systemic, topical, intraocular, intracerebral or intraspinal composition.

15. A method according to claim 10, wherein the disease, disorder or injury to be treated is an ophthalmic disease, disorder or injury.

16. A method according to claim 15, wherein the ophthalmic disease, disorder or injury is age related macular degeneration, retinitis pigmentosa, retinal detachments, retinal ischemia, acute retinopathies associated with trauma, inflammatory mediated degenerations, post-surgical complications, the damage associated with laser therapy including photodynamic therapy (PDT), or surgical light induced iatrogenic retinopathy.

17. A method according to claim 10, wherein the disease, disorder or injury to be treated is a brain or spinal cord disease or disorder.

18. A method according to claim 17, wherein the brain or spinal cord disease, disorder or injury is stroke, head trauma epilepsy and other seizure disorders, Alzheimer's disease, Huntington's disease, Lou Gehrig's disease (ALS) and other diseases, disorders or injuries where excitotoxic events are known to participate.

* * * * *